(12) United States Patent
Putzig

(10) Patent No.: US 7,122,690 B1
(45) Date of Patent: Oct. 17, 2006

(54) PROCESS TO PREPARE METAL COMPLEX OF N,N-BIS(2-HYDROXYETHYL)GLYCINE

(75) Inventor: Donald Edward Putzig, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/353,770

(22) Filed: Feb. 14, 2006

(51) Int. Cl.
*C07F 7/00* (2006.01)

(52) U.S. Cl. .......................... 556/55; 556/56

(58) Field of Classification Search .......... 556/55, 556/56
See application file for complete search history.

(56) References Cited

U.S. PATENT DOCUMENTS

| | | |
|---|---|---|
| 3,888,312 A | 6/1975 | Tiner et al. |
| 4,460,751 A | 7/1984 | Hanlon et al. |
| 4,512,407 A | 4/1985 | Friedman |
| 4,534,870 A | 8/1985 | Williams |
| 4,553,601 A | 11/1985 | Almond et al. |
| 4,579,670 A | 4/1986 | Payne |
| 4,635,727 A | 1/1987 | Anderson et al. |
| 4,649,999 A | 3/1987 | Sandy et al. |
| 4,657,081 A | 4/1987 | Hodge |
| 4,676,930 A | 6/1987 | Shu et al. |
| 4,683,068 A | 7/1987 | Kucera |
| 4,686,052 A | 8/1987 | Baranet et al. |
| 4,702,848 A | 10/1987 | Payne |
| 4,749,041 A | 6/1988 | Hodge |
| 4,797,216 A | 1/1989 | Hodge |
| 4,798,902 A | 1/1989 | Putrig |
| 4,799,550 A | 1/1989 | Harris et al. |
| 4,801,389 A | 1/1989 | Brannon et al. |
| 4,808,739 A | 2/1989 | Putzig et al. |
| 4,885,103 A | 12/1989 | Putzig et al. |
| 4,927,955 A | 5/1990 | Boigegrain et al. |
| 4,982,793 A | 1/1991 | Holtmyer et al. |
| 4,996,336 A | 2/1991 | Putzig et al. |
| 5,007,481 A | 4/1991 | Williams et al. |
| 5,036,919 A | 8/1991 | Thomas et al. |
| 5,067,565 A | 11/1991 | Holtmyer et al. |
| 5,089,149 A | 2/1992 | Ridland et al. |
| 5,106,518 A | 4/1992 | Cooney et al. |
| 5,305,832 A | 4/1994 | Gupta et al. |
| 5,614,475 A | 3/1997 | Moorhouse et al. |
| 5,773,638 A | 6/1998 | Dawson et al. |
| 5,975,206 A | 11/1999 | Woo et al. |
| 5,981,447 A | 11/1999 | Chang et al. |
| 6,017,855 A | 1/2000 | Dawson et al. |
| 6,046,140 A | 4/2000 | Woo et al. |
| 6,165,947 A | 12/2000 | Chang et al. |
| 6,186,235 B1 | 2/2001 | Tijon-Joe-Pin et al. |
| 6,213,213 B1 | 4/2001 | Van Batenburg et al. |
| 6,227,295 B1 | 5/2001 | Mitchell et al. |
| 6,242,390 B1 | 6/2001 | Mitchell et al. |
| 6,248,699 B1 | 6/2001 | Subramanian et al. |
| 6,387,986 B1 | 5/2002 | Moradi-Araghi et al. |
| 6,620,341 B1 | 9/2003 | Verma et al. |
| 6,737,386 B1 | 5/2004 | Moorhouse et al. |
| 6,739,806 B1 | 5/2004 | Szymanski et al. |
| 2004/0072700 A1 | 4/2004 | Gupta et al. |
| 2004/0116735 A1 | 6/2004 | Ward et al. |
| 2004/0152602 A1 | 8/2004 | Boles |
| 2004/0163813 A1 | 8/2004 | Slabaugh et al. |

FOREIGN PATENT DOCUMENTS

DE 4307709 9/1994

OTHER PUBLICATIONS

Cao et al., Chemical Abstracts, vol. 119, Abstract No. 139417, 1993.*

* cited by examiner

*Primary Examiner*—Porfirio Nazario-Gonzalez

(57) ABSTRACT

Metal complexes of titanium and zirconium with N,N-bis (2-hydroxyethyl)glycine are provided, and more particularly to an improved process to prepare the titanium and zirconium complexes of N,N-bis(2-hydroxyethyl)glycine. Such complexes are used in oil well fracturing and plugging applications.

17 Claims, 3 Drawing Sheets

PROCESS TO PREPARE METAL COMPLEX OF N,N-BIS(2-HYDROXYETHYL)GLYCINE

FIELD OF THE INVENTION

This invention relates to zirconium and titanium complexes which are useful as cross-linking agents in oil well fracturing and plugging applications, and more particularly to an improved process to prepare zirconium or titanium complex of N,N-bis(2-hydroxyethyl)glycine.

BACKGROUND OF THE INVENTION

The production of oil and natural gas from an underground well (subterranean formation) can be stimulated by a technique called hydraulic fracturing, in which a viscous fluid composition (fracturing fluid) containing a suspended proppant (e.g., sand, bauxite) is introduced into an oil or gas well at a flow rate and a pressure which create or extend a fracture into the oil- or gas-containing formation. The proppant is carried into the fracture by the fluid composition and prevents closure of the formation after pressure is released. Leak-off of the fluid composition into the formation is limited by the composition's fluid viscosity. Fluid viscosity also permits suspension of the proppant in the composition during the fracturing operation. Cross-linking agents, such as borates, titanates or zirconates are usually incorporated into the composition to control viscosity.

Putzig, et al., in U.S. Pat. Nos. 4,808,739 and 4,885,103, disclose N,N-bis-(2-hydroxyethyl)glycine/metal chelates and their use in plugging permeable subterranean zones and leaks. In U.S. Pat. No. 4,996,336, Putzig, et al. disclose a process for preparing a metal chelate by reacting N,N-bis-(2-hydroxyethyl)-glycine (BHET) with a titanium halide, titanium oxyhalide, zirconium halide, zirconium oxyhalide, tetraalkyl zirconate, or a certain tetraalkoxy (2-hydroxyethyl)glycine/metal chelate.

BHET may be produced by a number of routes, including the condensation of ethylene oxide with glycine, the condensation of chloroacetic acid with diethanolamine, the hydrolysis of N,N-bis(2-hydroxyethyl)-acetonitrile, and the hydrolysis of 4-(2-hydroxyethyl)-2-morpholinone. BHET has a number of small-volume uses in the biological and research fields, applications for which a high purity is generally required. It is available commercially, but generally at a high price.

The condensation of chloroacetic acid with diethanolamine to produce BHET is described in Kromov-Borisov and Remizov, in *Zhur. Obshchei Khim.*, 1953, 23, 598. Monochloroacetic acid was dissolved in water and neutralized with sodium hydroxide. The resulting solution of sodium monochloroacetate was added to diethanolamine and the mixture boiled and refluxed 3 to 4 hours. Khromov-Borisov and Remizov teach an extensive process comprising several steps to purify and isolate the product from the process solution. These steps are time-intensive and expensive. However, impurities, including unreacted starting materials and impurities generated in the process can interfere with formation and performance of a zirconium cross-linking agent prepared from the product of the process. For example, glycolic acid can be formed as a byproduct in the reaction by hydrolysis of chloroacetic acid or sodium chloroacetate. In some cases, this can be as high as 10–15%. Not only is there yield loss but also performance of the metal complex is adversely affected and made variable, depending on the extent and amount of impurities present, rather than consistent across batches of product. It is known that glycolic acid-based cross-linking agents result in a faster cross-linking rate than those based on BHET.

Gump, et al., in *J. Org. Chem.*, 1959, 24, 712–14, disclose preparation of BHET using the process as described by Khromov-Borisov and Remizov, but added that: "In order to obtain satisfactory yields, refluxing of the mixture should be carried out for 24 hr. instead of 3 to 4 hr."

There is a need for a process for making the zirconium or titanium salts of BHET without the above cumbersome, time-consuming and costly methods required for optimizing BHET yield, purification and isolation.

SUMMARY OF THE INVENTION

The present invention provides a process to prepare a metal chelate. Specifically, the chelating ligand is N,N-bis(2-hydroxyethyl)glycine. More specifically, the process comprises the steps of (a) contacting diethanolamine with chloroacetic acid or its alkali metal salt, such as sodium chloroacetate, in aqueous solution and (b) without isolating or purifying the product of step (a), contacting the product of step (a) with a metal complex wherein the metal is titanium or zirconium.

DETAILED DESCRIPTION OF THE INVENTION

Figure 1:
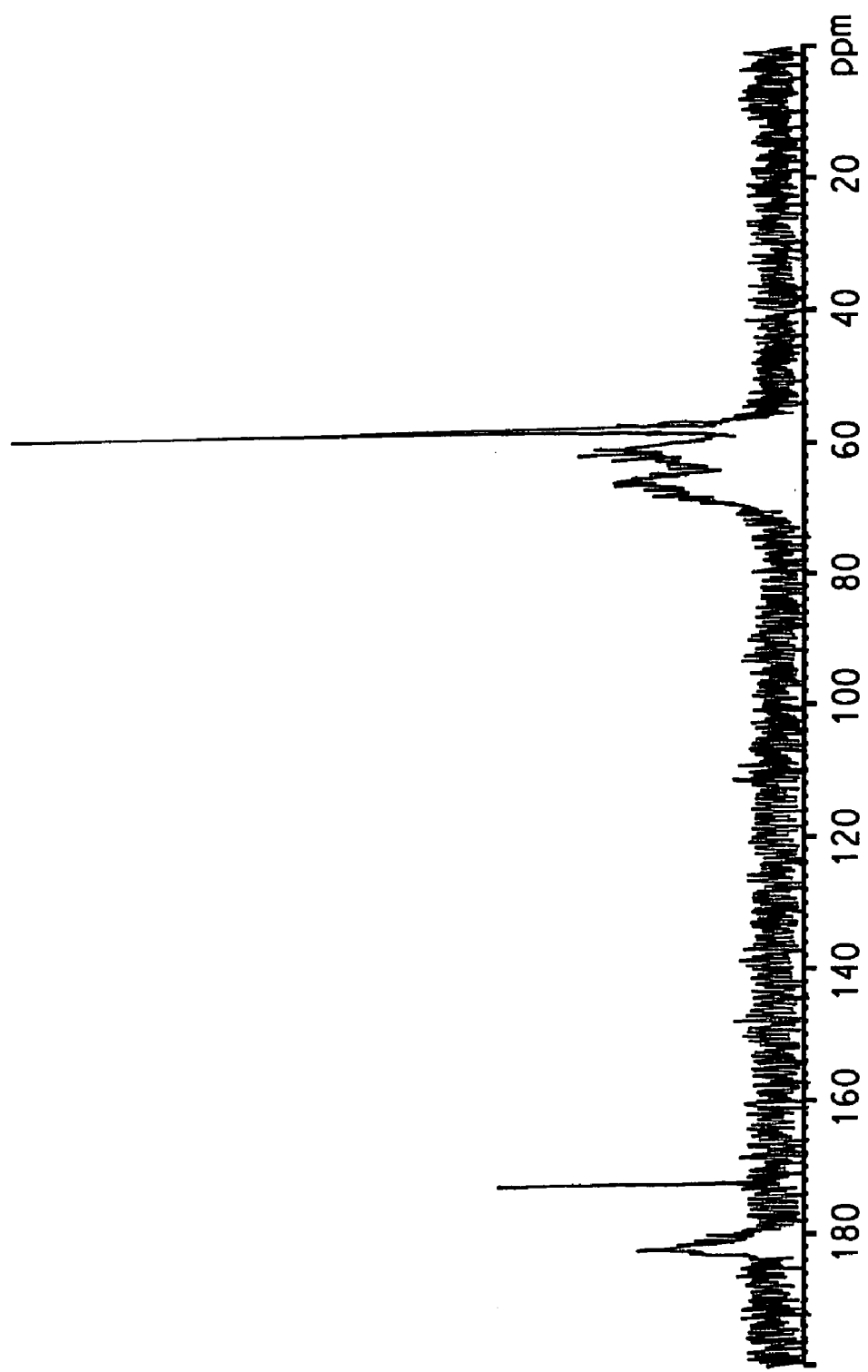
FIG. 1 is the $^{13}C$ NMR spectrum of the product of Example 1 made with inventive process for BHET solution.

The first step of this process is the preparation of N,N-bis(2-hydroxyethyl)glycine or "BHET". This step is carried out by the reaction of chloroacetic acid or its alkali metal salt with diethanolamine in an aqueous solution to form a reaction product. The reaction product comprises BHET in solution.

The alkali metal salt is typically lithium, sodium or potassium, with the sodium salt being preferred. Preferably, an equimolar amount of chloroacetic acid or its salt and diethanolamine are used. While other temperatures may be used, this first step is conveniently carried out at the boil, about 100° C. Although the reaction is essentially complete in about 3 hours, better yields of BHET are obtained if the reaction is extended up to about 10 hours. Thus, the typical reaction time for this first step is 3 to 10 hours. It is desirable to stop the reaction after 10 hours to avoid formation of undesirable degradation products, which form if the reaction time is prolonged. The presence of degradation products causes variation in rate of cross-linking of the metal chelate produced in the process of this invention. Deviating from the times, temperatures and molar ratio set forth above will increase the amount of impurities, such as glycolic acid in the product. It is recognized that many variations may be made within the ranges of conditions specified by those skilled in the art.

The second step of the inventive process is contacting the reaction product from the first step, without isolating or purifying BHET from the reaction product, with a metal complex of titanium or zirconium to produce a water-soluble metal chelate of titanium or zirconium.

The metal complex is typically a titanium or zirconium alkoxide or titanium or zirconium halide. Titanium and zirconium alkoxides may also be referred to as titanium and zirconium esters or as alkyl titanate and alkyl zirconate esters. For example, suitable titanium and zirconium alkoxides include $Ti(OR)_4$ or $Zr(OR)_4$ wherein R is an alkyl group having 1–12 carbon atoms. Titanium and zirconium halides include oxyhalides. Suitable titanium and zirconium halides include $TiCl_4$, $ZrCl_4$, $TiOCl_2$ or $ZrOCl_2$. $ZrOCl_2$ is preferred. When the metal complex is $ZrOCl_2$, it may be used as such or it may be generated in situ by reacting $ZrCl_4$ with water.

While any molar ratio may be used, generally, one or two molar equivalents of BHET per molar equivalent of metal complex are used.

The reaction of the titanium or zirconium alkoxide or halide with BHET may be performed over a range of temperatures. Generally, the temperature is between 15° C. and 100° C., i.e., up to the boiling point of water, preferably between 20° C. and 60° C.

The water-soluble metal chelate of BHET and titanium or zirconium prepared according to the process of this invention can be used in a hydraulic fracturing process in which one or more fractures is created or extended in an oil- or gas-containing subterranean formation which comprises introducing a cross-linked gel formed from a solvatable polysaccharide or, the reactive components to produce said cross-linked gel, into the formation at a flow rate and pressure sufficient to create or extend such a fracture. The water-soluble metal chelate of titanium or zirconium prepared according to the process of this invention can also be used in a process for selectively plugging permeable zones in a subterranean formation or for plugging subterranean leaks which process comprises injecting into or producing in the permeable zone or the site of the subterranean leak, a cross-linked gel formed from a solvatable polysaccharide. The cross-linking agent used in preparing the cross-linked gel in each process is the water-soluble metal chelate of titanium or zirconium prepared according to the process of this invention.

Other components can be added to produce the cross-linked gel as are known to those skilled in the art, such as delay agents, stabilizing agents, buffers, and the like.

EXAMPLES

The following Examples are given in further illustration of the invention but not by way of limitation. Preparation of the compositions in the Examples were carried out in a closed vessel equipped with an agitator, thermometer, condenser, nitrogen inlet and dropping funnel. Unless specified otherwise, percentages are given by weight.

Comparative Example A

A 5 liter flask was charged with 332 g of N,N-bis(2-hydroxyethyl)glycine, BHET (available from SigmaAldrich, St. Louis, Mo.) and 545 g of water. The mixture was heated to 40° C. to produce a solution. The solution was cooled to 5° C. and then zirconium oxychloride, 30% aqueous solution (1232.4 g), was added dropwise to the solution/reaction mass, while vigorously stirring at a temperature of 5–20° C. When addition was complete, the reaction mass was stirred for 1 hour and then neutralized with 20% sodium hydroxide solution to pH 7.5. The temperature was held at 5–20° C. during this neutralization. A total of 3080 g of a solution of the 1:1 BHET complex of zirconium was isolated. The solution contained 6.12% zirconium.

Example 1

A 5 liter flask was charged with 237 g of sodium chloroacetate and 422 g of water to provide a mixture. The mixture was heated to 40° C. to produce a solution. 218 g of diethanolamine was added dropwise to the solution over 30 minutes. The solution was then heated to 100° C. and held at this temperature for 10 hours, after which it was cooled to 5° C. Zirconium oxychloride, 30% aqueous solution (1232.4 g), was added dropwise to the solution/reaction mass, while vigorously stirring at a temperature of 5–20° C. When addition was complete, the reaction mass was stirred for 1 hour and then neutralized with 20% sodium hydroxide solution to pH 7.5. The temperature was held at 5–20° C. during this neutralization. A total of 3087 g of a solution of the 1:1 BHET complex of zirconium was isolated. The solution contained 6.12% zirconium.

Example 2

The procedure of Example 1 was repeated except 616.2 g of 30% aqueous solution of zirconium oxychloride was used to produce a product with a 2:1 ratio of BHET to zirconium.

Analysis

Figure 2:
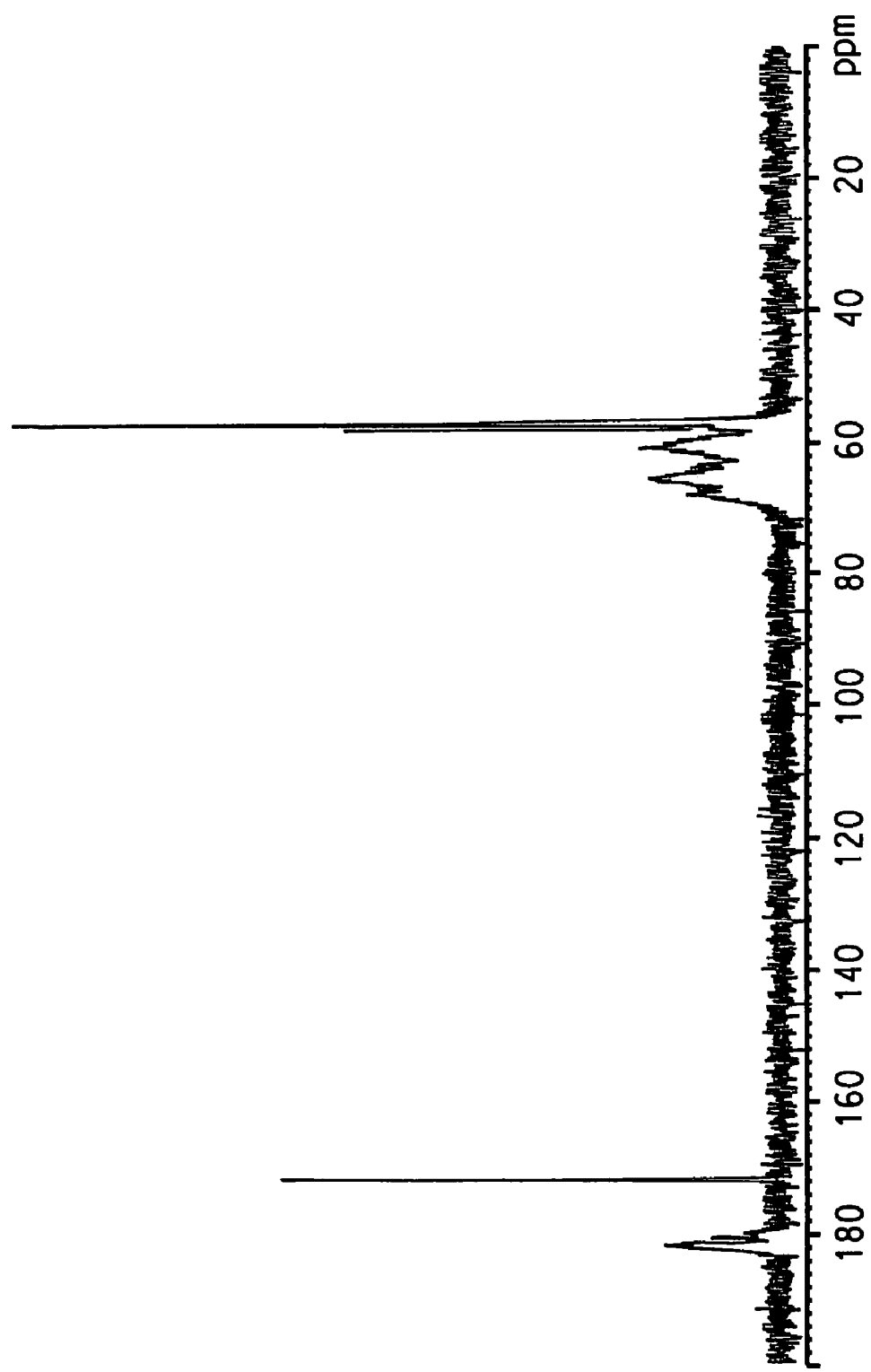
FIG. 2 is the $^{13}C$ NMR spectrum of the product of Comparative Example A made with commercially prepared BHET.

The $^{13}C$ Nuclear Magnetic Resonance (NMR) spectrum of the 1:1 BHET complex of zirconium as prepared above in Example 1 is shown in FIG. 1. The $^{13}C$ Nuclear Magnetic Resonance (NMR) spectrum of the 1:1 BHET complex of zirconium as prepared above in Comparative Example A using commercially available BHET is shown in FIG. 2. Each $^{13}C$ NMR spectrum was generated using a Varian INOVA 500 Mhz instrument (available from Varian, Inc., Palo Alto, Calif.). From these Figures, it is surprisingly seen that the product of Example 1 and the product of Comparative Example A were essentially identical, despite only a 10 hour reaction period to produce the BHET and with no purification or isolation prior to introducing the zirconium complex.

Example 3

Figure 3:
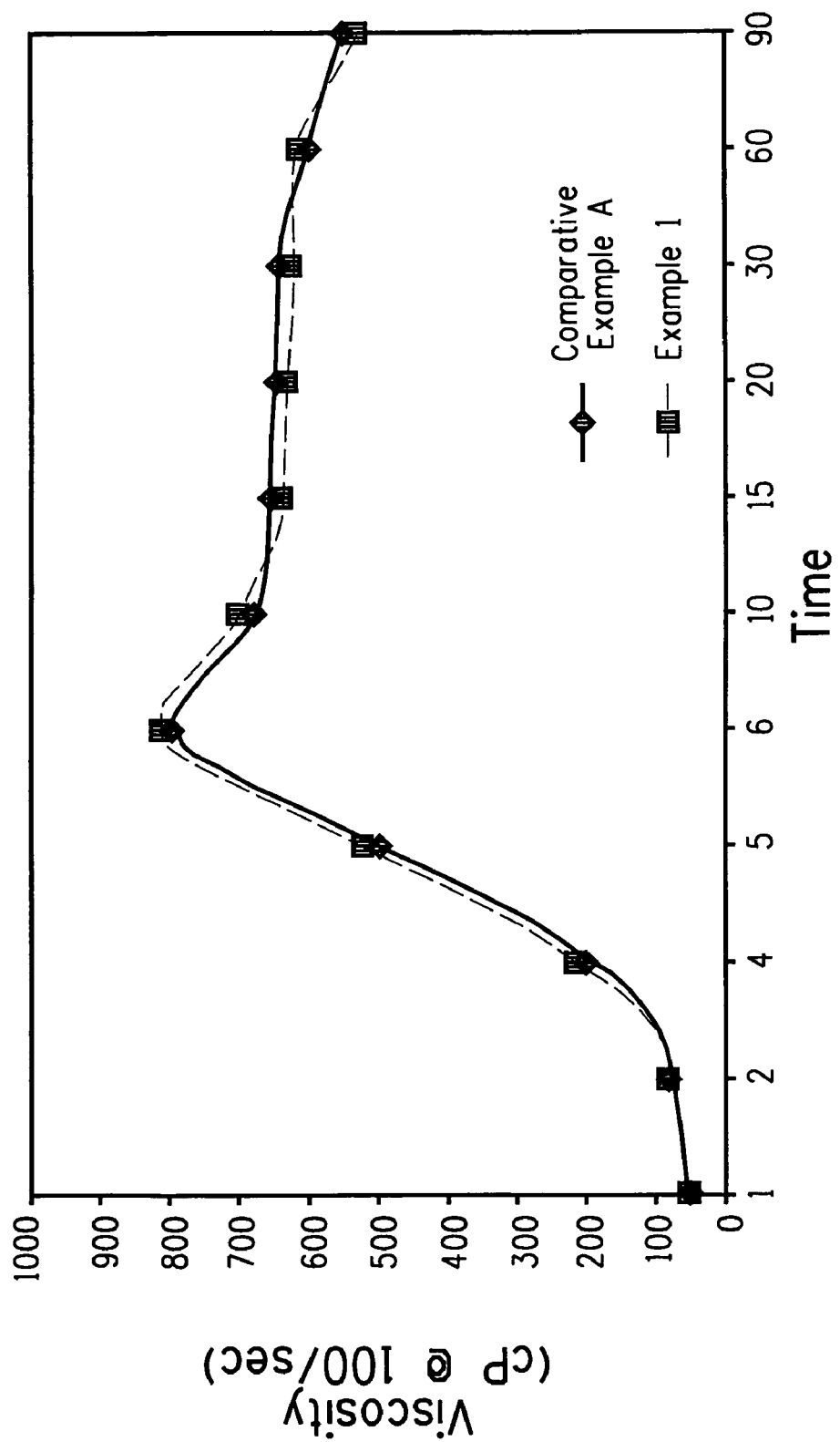
FIG. 3 is a graph illustrating cross-linking properties of the products of Example 1 and Comparative Example A.

The cross-linking properties of the product of Comparative Example A and Example 1 were tested using the following procedure. A 30 lb/1000 gal solution (0.03 g/ml) of carboxymethyl hydroxypropylguar (CMHPG, available from Economy Polymers, Houston, Tex.) was prepared by dissolving 2.7 g of CMHPG in 750 ml of water containing 0.75 ml of a 50 weight % solution of tetramethylammonium chloride clay stabilizer (available from SigmaAldrich, St. Louis, Mo.). The pH of the solution was adjusted to 11.0 with sodium hydroxide and then agitated in a Waring blender for 30 minutes, resulting in a hydrated base gel. The hydrated base gel was added to a 1500 ml beaker. The cross-linking solution of Comparative Example A or Example 1 (0.75 ml) was added with vigorous mixing over a period of one minute to produce a cross-linked gel. A 25-ml sample of the cross-linked gel was placed in a cup of a Fann 50C Viscometer (available from the Fann Instrument Company, Houston, Tex.) equipped with an R-1, B-2 bob. The viscosity of the gel using each of the cross-linking solutions was measured in centipoise (cP) at 275° F. (135° C.) at 100 reciprocal seconds of shear. The viscosity as measured over a 90 minute period is in FIG. 3. As can be seen in FIG. 3, the product of Example 1, in which the reaction product of sodium chloroacetate and diethanolamine was reacted with zirconium oxychloride performs as well as the product of Comparative Example A, in which purified BHET was reacted with zirconium oxychloride. The products of Example 1 and Comparative Example A have similar rates of viscosity development, which is 6 minutes to maximum viscosity and viscosity retention of 550 cP after 90 minutes at the same temperature (275° F. or 135° C.) and shear rate (100 sec-1). Thus, the process of this invention provides a BHET product from which a metal cross-linking agent can be made of sufficient quality to provide desired performance in product complex.

What is claimed is:

1. A process for preparing a metal chelate which comprises (a) contacting diethanolamine with chloroacetic acid or its alkali metal salt in aqueous media and (b) contacting the product of step (a), without isolating or purifying the product of step (a), with a metal complex wherein the metal is titanium or zirconium.

2. The process of claim 1 wherein in step (a), diethanolamine and chloroacetic acid or its alkali metal salt are contacted in equimolar amounts.

3. The process of claim 1 wherein step (a) is performed at a temperature of about 100° C.

4. The process of claim 3 wherein step (a) is performed for a period of at least 3 hours up to about 10 hours.

5. The process of claim 1 wherein the metal complex is selected from the group consisting of metal halides, metal oxyhalides, and metal alkoxides.

6. The process of claim 5 wherein the metal is titanium.

7. The process of claim 6 wherein the metal complex is a titanium alkoxide.

8. The process of claim 6 wherein the metal complex is a titanium halide.

9. The process of claim 5 wherein the metal is zirconium.

10. The process of claim 9 wherein the metal complex is a zirconium alkoxide.

11. The process of claim 9 wherein the metal complex is a zirconium halide.

12. The process of claim 11 wherein the metal complex is zirconium oxychloride.

13. The process of claim 3 wherein the temperature in step (b) is 15 to 100° C.

14. The process of claim 13 wherein the temperature in step (b) is 20 to 60° C.

15. The process of claim 1 wherein in step (a), an alkali metal salt of chloroacetic acid is used.

16. The process of claim 15 wherein the alkali metal salt is sodium.

17. The process of claim 1 wherein in step (a) chloroacetic acid is used.

* * * * *